US008389931B2

(12) United States Patent
Jackson et al.

(10) Patent No.: US 8,389,931 B2
(45) Date of Patent: Mar. 5, 2013

(54) METHOD FOR SEQUENCING PEPTIDES AND PROTEINS USING METASTABLE-ACTIVATED DISSOCIATION MASS SPECTROMETRY

(75) Inventors: Glen P. Jackson, Athens, OH (US); Olivier Collin, Athens, OH (US)

(73) Assignee: Ohio University, Athens, OH (US)

( * ) Notice: Subject to any disclaimer, the term of this patent is extended or adjusted under 35 U.S.C. 154(b) by 108 days.

(21) Appl. No.: 12/955,168

(22) Filed: Nov. 29, 2010

(65) Prior Publication Data

US 2011/0186725 A1 Aug. 4, 2011

Related U.S. Application Data

(63) Continuation of application No. 11/916,445, filed as application No. PCT/US2006/021620 on Jun. 5, 2006, now abandoned.

(60) Provisional application No. 60/687,584, filed on Jun. 3, 2005.

(51) Int. Cl.
*H01J 49/00* (2006.01)
(52) U.S. Cl. ......... 250/282; 250/281; 250/287; 250/288
(58) Field of Classification Search ............... 250/281, 250/282, 283, 288, 290
See application file for complete search history.

(56) References Cited

U.S. PATENT DOCUMENTS

| | | | | |
|---|---|---|---|---|
| 6,124,675 A | * | 9/2000 | Bertrand et al. | 315/111.91 |
| 6,843,375 B2 | | 1/2005 | Scheidemann et al. | |
| 6,891,154 B2 | * | 5/2005 | Zhu et al. | 250/282 |
| 7,170,051 B2 | * | 1/2007 | Berkout et al. | 250/281 |
| 7,397,029 B2 | * | 7/2008 | Berkout et al. | 250/288 |
| 7,586,092 B1 | * | 9/2009 | Karpetsky | 250/288 |
| 2004/0041089 A1 | * | 3/2004 | Zhu et al. | 250/282 |
| 2005/0056775 A1 | * | 3/2005 | Cody et al. | 250/281 |
| 2008/0217526 A1 | * | 9/2008 | Colby et al. | 250/282 |
| 2011/0186725 A1 | * | 8/2011 | Jackson et al. | 250/282 |
| 2011/0215237 A1 | * | 9/2011 | Bateman | 250/282 |

OTHER PUBLICATIONS

Written Opinion of the International Searching Authority for WO Application No. PCT/US2006/021620, dated Jun. 16, 2008.
International Preliminary Report on Patentability for WO Application No. PCT/US2006/021620, dated Jul. 8, 2008.

* cited by examiner

*Primary Examiner* — Michael Maskell
(74) *Attorney, Agent, or Firm* — Calfee, Halter & Griswold LLP

(57) ABSTRACT

Methods for fragmentation of large molecular ions, including proteins, nucleic acids, dendromers, and nanomaterials, compatible with several mass spectrometric techniques. The methods involve providing a gas-phase ion and allowing the gas phase ion to undergo collisions with metastable states of noble gases or nitrogen gas.

10 Claims, 3 Drawing Sheets

METHOD FOR SEQUENCING PEPTIDES AND PROTEINS USING METASTABLE-ACTIVATED DISSOCIATION MASS SPECTROMETRY

CROSS-REFERENCE TO RELATED APPLICATIONS

This application is a continuation of application Ser. No. 11/916,445, filed Jun. 16, 2008, which is the national stage of International Application No. PCT/US06/21620, filed Jun. 5, 2006, which claims the benefit of U.S. Provisional Patent Application No. 60/687,584, filed Jun. 3, 2005, the entirety of each of which are incorporated herein by reference

BACKGROUND

Tandem mass spectrometry summarizes a broad range of techniques whereby mass selected ions are subjected to a second (or more) level or mass spectrometric analysis. Such is the social and technological importance of tandem mass spectrometry that to date more than a million blood and plasma samples from newborns have been tested for various disorders using such devices. Tandem mass spectrometry is also a central technology for proteomics and other important areas of macromolecular identification, such as drug and metabolite monitoring for forensics.

At present, there are essentially three physical processes by which the internal energy of gas phase ions is raised above the dissociation threshold: 1) collisions with atoms, molecules, or surfaces 2) photodissociation, and 3) dissociative recombination of positively and negatively charged species. Of these methods, collision activated dissociation (CAD), also called collision induced dissociation (CID), is the most widely practiced method. Although collisional activation has many advantages over alternative activation methods, the major limitation of collisional activation is in its ineffectiveness at dissociating high mass ions (such as biomolecules) and molecules with high barriers for dissociation.

The ineffectiveness of CAD for high mass ions stems from a number of factors including 1) inefficient conversion of kinetic to internal energy and 2) increased number of degrees of freedom. In addition, CAD of biological ions often results in the loss of one or more small neutral losses such as water or ammonia with the consequence of uninformative fragmentation patterns. Wide-band excitation has been described recently to attempt to overcome these difficulties, but other problems remain. Significant ion losses, and subsequent decreases in sensitivity are notable in CAD devices because reagent ions and fragment ions are often scattered during, or inefficiently collected, after the collisional processes. Also, as the size of the reagent ion increases, so does the number of fragment ions over which the residual charges must be spread. Fragmentation into a large number of channels leads to decreased sensitivity and may prevent the ability to perform $MS^n$ (n>2) fragmentation analyses.

Surface-induced dissociation (SID) has been applied to ion beam, quadrupole, and ICR-type instruments and shows many improvements over CAD for dissociating large biomolecules. However, significant complications arise from surface sputtering, surface reactions, ion losses and collision angle effects.

In the "top down" approach to proteomics, the dissociation of biomolecules in the kDa-MDa mass range is necessary, and this can only be achieved using CAD if it is used in combination with significant proton attachments to effect coulombic repulsions within the biomolecules. A more promising approach to fragmenting large biomolecules has been through electron capture dissociation (ECD) in FT-ICR instruments. This particular technique seems restricted to ICR instruments, however, and may not be applicable to more commonly available mass spectrometers such as quadrupole based systems. There is also the inherent requirement for multiple charges on the reagent ion, as neutralization by an electron reduces the overall charge of the reagent with each capture. For large mono-positive ions, such as dendromers or polymers, ECD may not be applicable.

Moreover, commercial instruments available today typically cannot directly determine the amino acid sequence of large peptides and whole proteins (e.g. >3 kDa). This is primarily due to the difficulty of breaking apart large ions within mass spectrometers, but also due to the inability to control where fragmentation takes place within the bio-ions. If these limitations regarding the fragmentation of large biomolecules could be overcome, biomedical research that depended on protein identification could be considerably accelerated.

Accordingly, there exists a need for additional or complementary methods for dissociating macromolecular ions in the gas phase. This need is especially essential for large biomolecules of interest to human health, national security and forensic applications wherein existing techniques are ineffective for providing conclusive and reproducible results.

SUMMARY

Provided are methods for the fragmentation of large molecular ions, such as proteins, nucleic acids, dendromers, and nanomaterials that are compatible with several mass spectrometric techniques, including quadrupole ion trap mass spectrometry. The methods comprise the steps providing a gas-phase ion and allowing the gas-phase ion to undergo collisions with metastable states of noble gases or $N_2$.

DETAILED DESCRIPTION

Figure 1:
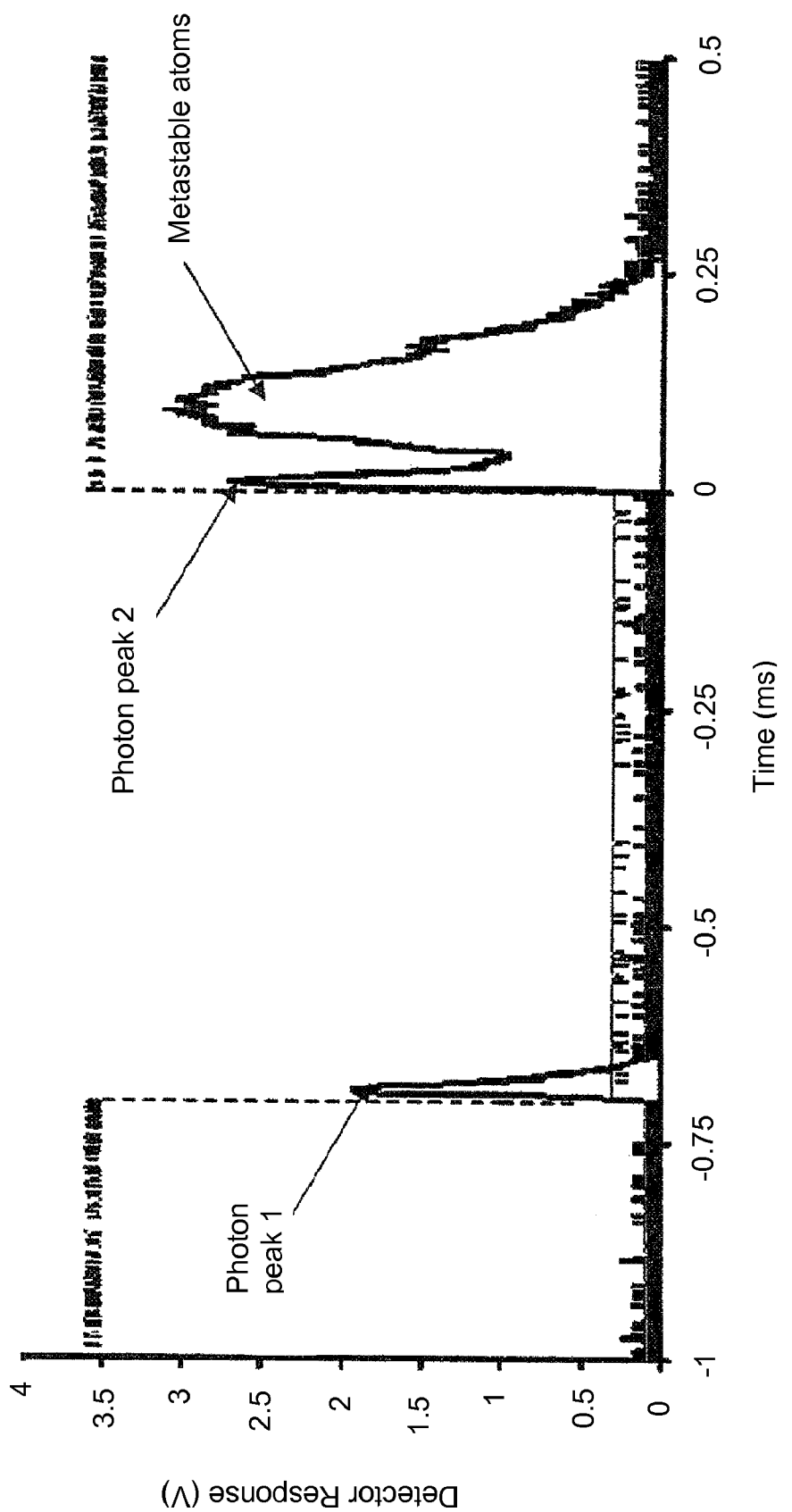
FIG. 1 shows the production of metastable argon atoms in a pulsed discharge source.

Provided herein is a new paradigm for inducing tandem mass spectrometry of gas-phase ions by allowing the ions to undergo controlled collisions with metastable states of nobles gases or $N_2$. Reactions involving metastable atoms with charged reagents, such as ions stored in ion trapping instruments, offer significant advantages over existing methods of ion activation. Table 1 compares the activation method described herein to several practiced activation methods.

TABLE 1

Basic description of some practiced activation methods and the comparison to the method of activation described herein.*

| Activation method | Energy range | Instruments | Comments |
|---|---|---|---|
| PSD | Low | ReTOF | Metastable decay caused by excess internal energy from ionization. |
| CID (CAD) | Low | IT, FTICR, QqX | Controlled-energy (1-100 $eV_{lab}$) collisions with inert gases. |
| | High | TOF/TOF, sectors | Same, but keV energies. |
| SID | Low | XqQ, IT, FTICR | 1-100 $eV_{lab}$ collisions between ions and a metal or SAM surface. |
| | High | TOF/TOF, sectors | Same, but at keV energies. |
| ECD | Low | FTICR | Capture of low energy electrons by positive ions; radical ion chemistry follows. |
| IRMPD | Low | IT, FTICR | IR laser slowly raises internal energy of ions above dissociation thresholds |
| BIRD | Low | IT, FTICR | Heated systems used as IR source to achieve similar consequences as IRMPD. |
| MAD (this work) | Low or High | IT, FTICR, QqX | Metastable atoms with different energies used to excite or ionize ions. Radical ion chemistry may follow ionization. |

PSD = post-source decay;
CID = collision-induced dissociation;
CAD = collision-activated dissociation;
SID = Surface-induced dissociation;
ECD = electron capture dissociation;
IRMPD = infrared multiphoton dissociation;
BIRD = blackbody infrared radiative dissociation;
MAD = metastable-activated dissociation;
ReTOF = reflectron time-of-flight;
IT = linear or quadrupole ion trap;
FTICR = fourier transform ion cyclotron resonance;
QqX = mass selective quadrupole followed by rf-only multipole followed by any mass analyzer;
TOF/TOF tandem time of flight;
XqQ = any mass selective device followed by an rf-only multipole followed by a mass selective quadrupole;
SAM = self-assembled monolayer.

Of these activation methods, collision-activated dissociation (CAD), also called collision-induced dissociation (CID), is the most widely practiced method. CAD of peptides and small proteins has been extensively studied and the major fragmentation pathways are well known. Although CAD has many advantages over alternative activation methods, its major weakness is its ineffectiveness at dissociating molecules with high energy barriers for dissociation and high mass ions such as proteins. The methods described herein overcome these limitations and could open the door to sequencing large, intact proteins.

The ineffectiveness of CAD for high mass ions stems from two major factors: 1) inefficient conversion of kinetic to internal energy, and 2) increased number of degrees of freedom. In addition, CAD of biological ions, especially proteins, often results in the loss of one or more small neutral groups such as water or ammonia. In these cases, little or no structural information is obtained. Wide band excitation has been described recently to attempt to overcome these difficulties, but other challenges remain. For example, in CAD the precursor ions must be accelerated to enable higher-energy collisions to occur. In ion trap mass spectrometers, this often limits the sensitivity because of scattering of precursor ions and inefficient collection of product ions. Furthermore, as the size of the precursor ion increases, so does the number of fragment ions over which the residual charges must be distributed. Fragmentation into a large number of channels leads to decreased sensitivity and the inability to perform MS$^n$ (n>2). Although ion trap mass spectrometers dominate the market for sequencing peptides, there is room for additional or complementary methods for performing tandem mass spectrometry.

In the 'top down' approach to proteomics, the dissociation of biomolecules in the kDa-MDa range mass is necessary and this is oftentimes achieved using CAD in combination with significant proton attachments to cause coulombic repulsions within the biomolecules. It has been shown that the charge state of proteins undergoing CAD plays a significant yet unpredictable role in determining the fragmentation pathways. Work is progressing in the area of CAD of whole proteins, but the secondary and tertiary structures of large proteins seem to favor a select number of fragmentation pathways. Although whole proteins can be identified using CAD, complete sequence coverage is rarely obtained.

A recent approach to fragmenting large biomolecules has been through electron capture dissociation (ECD) in FT-ICR instruments. One advantage of ECD is the extensive fragmentation along the amide backbone, which has shown to generate more complete amino-acid sequence coverage of peptides. An exception is that ECD strongly favors certain fragmentation pathways, such as on the C-terminal side of Trp. Recently, ECD has been applied to radio frequency ion traps but does not yet seem to offer such promising results as ECD conducted in FT-ICR spectrometers. Because ECD seems to be most suitable to FT-ICR spectrometers, such expensive instrumentation will not be a financially viable option for most researchers. There is also an inherent requirement for ions to be positively- and preferably multiply-charged because electron capture is more favorable under these conditions. Obviously, ECD is not possible for negatively charged ions, which would exclude certain analyses such as DNA and proteins analyzed in negative-ion mode.

The above discussion shows that there is a clear and present need for complementary methods for dissociating bio-ions in the gas phase. This capability is especially needed for large biomolecules where existing techniques can struggle to be effective at providing conclusive and reproducible results. The ability to sequence large proteins would circumvent lengthy digestion, separation and purification procedures and would enable biomedical and clinical researchers to identify important proteins more rapidly. This new activation method described herein is compatible with both new and existing mass spectrometers and separation technologies.

Metastable atoms of noble gases occupy well known energy levels. Argon has two metastable states at 11.55 and 11.72 eV above the neutral ground state. Table 2 shows the energies of the metastable atoms of different noble gases. In the absence of collisions, metastable atoms can exist for several seconds, giving them time to find a collision partner. When a metastable atom collides with a neutral atom or molecule with a lower ionization potential than the metastable level, the metastable is capable of ionizing the neutral in a process called Penning Ionization (PI), $$M^* + AB \rightarrow M + AB^{*+} + e^-$$

Where M* is the metastable atom and AB is the neutral molecule. When energetically feasible, more than one in three collisions result in deexcitation in this manner. This is very efficient. If the metastable atom has more energy than the minimum required to ionize the neutral, the excess energy can be distributed between the kinetic energy and the internal energy of the products. The ejected electron tends to carry any significant kinetic energy and the newly generated molecular ion carries any excess internal energy.

Excess internal energy resulting from PI can lead to extensive fragmentation of polyatomic ions, $$M^* + AB \rightarrow M + AB^{*+} + e^- \rightarrow A^+ + B$$

whereas smaller molecules tend to display informative photoemission spectra, $$M^* + AB \rightarrow M + AB^{*+} + e^- \rightarrow AB^+ + h\nu$$

These basic phenomena have been known for decades, but until recently have not been utilized for the deliberate fragmentation of polyatomic species. By using different noble gases or diatomic molecules (such as $N_2$), it is possible to generate metastable atoms in a selective range of energies and thus provide Penning ionization reactions with tunable degrees of fragmentation. While reactions between metastable atoms and large macro-ions cannot be found in the literature, studies using the methods described herein suggest that in a collision between a gas-phase macro-ion and a metastable atom can yield two possible results, depending on the ionization potential of the ion: First, macro-ion/metastable collisions may result in subsequent ionization of the macro-ion. Reactions of this kind could continue until the $n^{th}$ IP of the macro-ion is greater than the energy level of the metastable in question. Second, macro-ion/metastable collisions may result in the internal excitation of the ion, with or without ionization. Multiple collisions of this kind could be used to increase the internal energy of the ion until the threshold energy for fragmentation is reached.

TABLE 2

Characteristics of metastable atoms of noble gases.*

| Atom | Electron configuration | State | Excitation energy (eV) | Lifetime (s) | Polarizability ($Å^3$) |
|---|---|---|---|---|---|
| He | 1s2s | $2^1S_0$ | 20.62 | ~0.02 | >9 |
|  |  | $2^3S_1$ | 19.82 | >7900 | 46.9 |

TABLE 2-continued

Characteristics of metastable atoms of noble gases.*

| Atom | Electron configuration | State | Excitation energy (eV) | Lifetime (s) | Polarizability ($Å^3$) |
|---|---|---|---|---|---|
| Ne | $2p^53s$ | $^3P_0$ | 16.72 | 430 |  |
|  |  | $^3P_2$ | 16.62 | 24.4 | 27.8 |
| Ar | $3p^54s$ | $^3P_0$ | 11.72 | 44.9 |  |
|  |  | $^3P_2$ | 11.55 | 55.9 | 47.9 |
| Kr | $4p^55s$ | $^3P_0$ | 10.56 | 0.49 |  |
|  |  | $^3P_2$ | 9.92 | 85 | 50.7 |
| Xe | $5p^56s$ | $^3P_0$ | 9.45 | 0.08 |  |
|  |  | $^3P_2$ | 8.32 | 150 | 63.6 |

In the first scenario above, repeated ionization reactions may benefit macro-ion analysis in several ways:

First, PI results in the ejection of a single electron and the generation of a radical positive ion. Radical ions are known to be considerably more reactive than proton-bound bio-ions, and the phenomenon may lead to rearrangements or fragmentations of the ion in question (such as McLafferty-type rearrangements). Because Penning ionization reactions are known to be electrophilic, ionization is likely to take place on a site such as a lone pair of electrons on an oxygen molecule of a carbonyl group. Therefore, when a protein or peptide ion is ionized by Penning ionization and the ion subsequently rearranged according to McLafferty-like rearrangement, amide cleavage would result and the products may provide amino acid sequence information for the reagent ion.

Second, increasing the charge state of the bio-ion increases the coulombic repulsions within the bio-ion. This facilitates unfolding and fragmentation of the bio-ion.

Third, a reagent ion with only one charge can undergo Penning ionization to provide two products with two charges distributed between them. It is possible that each of the product (fragment) ions could retain a charge, in which case each of the fragment ions can be detected in a mass-selective manner. In this case, one could recapture product ions and subject them to subsequent Penning-type reactions. This could lead to the ability to perform $MS^n$ experiments.

In the second scenario above, the energy deposited with each Penning excitation collision could be as high as 20 eV for the case of helium metastable atoms. For comparison, CAD of a 10 kDa bio-ion with argon as the collision gas would require at least 5200 eV in the lab frame, assuming a completely inelastic collision. Such energies are barely obtainable in laboratory-scale ion-beam apparatus, and certainly not in quadrupole or ICR based instruments. Multiple Penning collisions could build significant internal energy in the macro-ions depending, of course, on the balance between the radiative loss rate of the macro-ion and the collision rate with metastable.

A distinct advantage of Penning excitation and ionization over CAD or SID is that the kinetic energy of the reagent ions is virtually unaffected by Penning collisions. Scattering losses should be minimal and collection efficiencies of resulting fragments should be very high. Another potential advantage is that neutral fragments released during fragmentation could be re-ionized via PI reactions with new metastable atoms. This could provide another mechanism for improving the sensitivity of $MS^n$ experiments. An additional feature is that Penning-type reactions can take place with neutral molecules or positive or negatively charged ions. Ion-ion reactions and electron-capture reactions are more limited in their scope.

Very recent experiments exposing self-assembled monolayers (SAM) to metastable atoms in vacuum show that ionized fragments of the monolayer species are desorbed from the surface, indicating that the metastable collisions have very shallow surface interactions. In these experiments, C—H and C—C bond cleavages were made possible by collisions with metastable helium atoms and significant but uncharacterized structural changes were possible using metastable argon atoms.

Studies of collisions between metastable atoms with organic surfaces show that interactions of metastable atoms with large macro-ions may result in little more than ejection of $H^+$ or $CH_3+$ ions from the outermost surface of the macro-ion. In this "worst case scenario" the resulting surface modifications of trapped macro-ions could be determined by an accompanying activation technique (such as CAD). For peptides and proteins, this information is almost certain to provide valuable information regarding the exposed surfaces in the folded ions. The utility of metastable activated reactions to elucidate the composition of single stranded (ss) and double stranded (ds) DNA fragments is also be of interest. Penning ionization of ss or ds DNA may also enable sequencing information to be obtained. This would allow the identification of PCR products, for example. This has the potential to have a dramatic impact on DNA sequencing capabilities.

Experimental Approach

The first prototype instrument is currently being configured on a commercial platform ion trap mass spectrometer. Quadrupole ion traps (QITs) have demonstrated ability to obtain isolated charge states of macro-ions in the gas phase, and to store macro-ions for extended periods. QITs operate over a range of pressures compatible with metastable sources. A metastable atom source has been built and initial testing suggests that metastable atoms are successfully transferred to the trapping region.

FIG. 1 shows the result of an initial test of the metastable source, demonstrating the ability to form metastable atoms in the pulses or ~100 μs in width. The red line in FIG. 1 shows the voltage applied to tungsten wire in the discharge region. When it pulses to −600 V, a plasma is produced and photons are emitted. These are detected down-stream in the vacuum chamber by an electron multiplier. When the voltage returns to zero at "0" seconds, photons are emitted as a result of recombination and metastable atoms are subsequently formed. Two electrodes were used to prevent electrons and ions from reaching the detector, so only photons and highly energetic compounds can be detected. A double optical chopper is currently being installed to block the photons from reaching the detector (or ion trap) and thus will only allow ground-state and excited-state neutral atoms to reach the detector.

Figure 2:
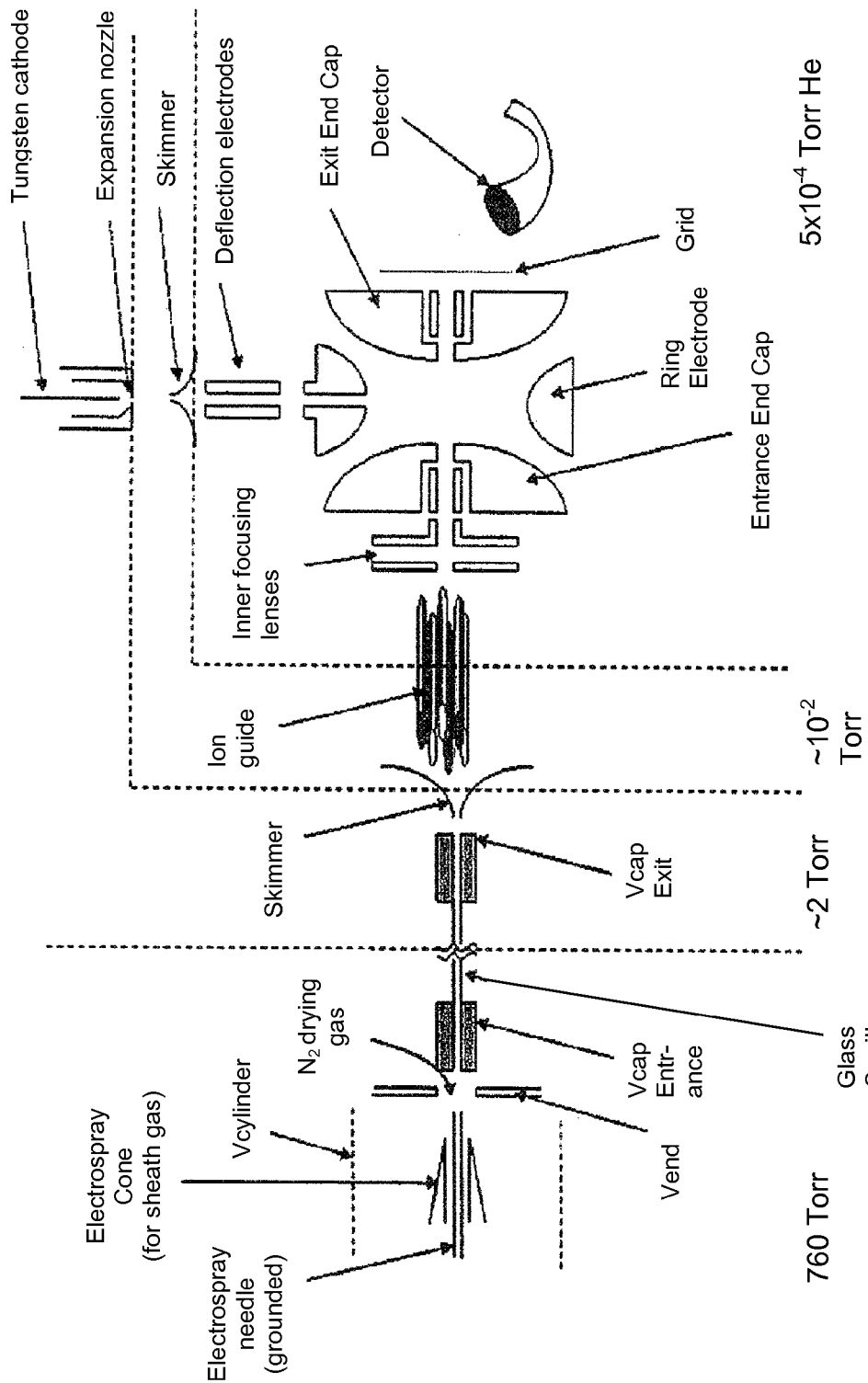
FIG. 2 shows a schematic for combining a metastable atom source with a quadrupole ion trap mass spectrometer to perform a metastable-activated dissociation mass spectrometry (MAD-MS) experiment.

In one embodiment, the source would be configured to the vacuum chamber of a quadrupole ion trap mass spectrometer and metastable ions would enter the trapping region through a small hole drilled through the ring electrode. Initial testing of the ion trap confirms that such a hole does not deleteriously affect the performance of the ion trap. A schematic of one possible configuration is shown in FIG. 2.

Figure 3:
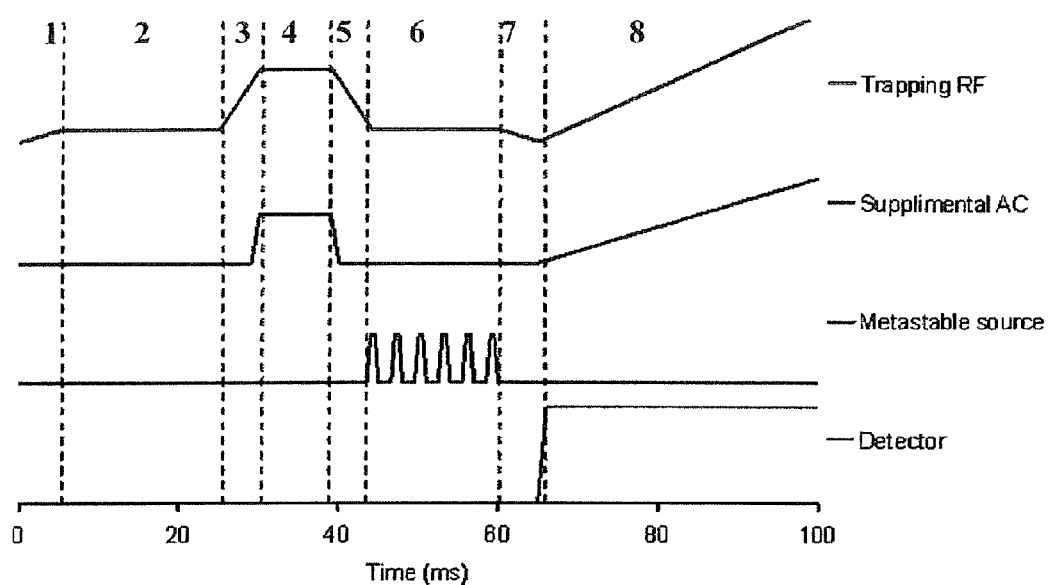
FIG. 3 shows the time sequence for a metastable-activated dissociation mass spectrometry (MAD-MS) experiment.

FIG. 3 shows a typical time sequence of different electrical components pertinent to the experiment.

The time sequence shown in just one example or a way in which metastable-activated dissociation can be competed. Time sequences for ion-ion reactions, ion-molecule reactions, CID, IRMPD (infrared multi-photon dissociation) may be added. The time sequences are labeled as follows: 1) pre-ion accumulation period; 2) ion accumulation from ESI/APCI/MALDI ion source; 3) pre-isolation; 4) isolation of reagent ion of interest; 5) pre-MAD; 6) metastable-activated dissociation (MAD) of reagent ion; 7) pre-detection; 8) detection of product ions.

In step 6, a metastable-atom-beam of selectable pulse-duration would be introduced to the center of the trapping region to effect excitation/ionization of the trapped macro-ions. In some cases, it may be necessary to send multiple pulses of metastable atoms to effect dissociation or other reaction with the trapped ions. The macro-ions would be formed using a commercial interface, most probably an electrospray, nanospray, or (AP) MALDI source.

Applications

Tandem mass spectrometry of macro-ions is just one example of a highly beneficial application involving metastable atom activation. Other applications involving bio-ions include 'top down' and 'bottom up' proteomics, generic screening, and forensic applications, such as bacterial and viral screening. Any current application of tandem mass spectrometry using one of the activation methods identified in Table 1 could in principle be achieved using this new method of activation. To date, CAD of single and double stranded DNA material has provided very challenging interpretation because backbone cleavages are not as frequent or as predictable as for peptide fragmentation. Metastable-activated dissociation of DNA analogues could be possible using this approach and could lead to the ability to sequence DNA. Other macro-ion applications include the structural analyses of polymers, dendromers and nano-materials, all of which could undergo surface modifications or fragmentation/rearrangement upon absorbing energy via Penning-type collisions.

In addition to Penning-type collisions the metastable source could be easily configured as a source for positive ions or electrons for ion-ion reactions in the trapping region. Multiple ion, electron or metastable sources may be configured in a single device to provide additional dimensions of flexibility for macro-molecular studies, forensic and bio-ion applications. An example would be to perform ion-ion reactions prior to metastable-ion reactions in order to obtain the macro-ion in the desired charge state in maximum abundance prior to MAD tandem mass spectrometry.

The vast literature on metastable atom-neutral collisions (from atoms to liquids and large surfaces) suggests that a metastable atom-bio-ion collision will result in one of two possible outcomes: 1) A collision will result in ionization of the bio-ion (B),

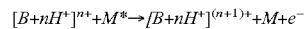

This would lead to the generation of a radical cation, which is known to be more reactive than a protonated, even electron cation. This type of process is often accompanied by internal excitation, rearrangement and subsequent fragmentation; or 2) A collision will lead to excitation of the bio-ion without ionization.

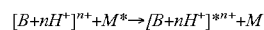

Multiple collisions of this kind could be used to increase the internal energy of the macro-ions until the fragmentation threshold energy is reached.

The reaction products will depend on the energy of the metastable atom used, the IP of the target and the reaction chemistry involved. Preliminary data on neutral amides shows that metastables tend to ionize the carbonyl oxygen atoms of small amides; we hypothesize that charged amides will react similarly. As discussed above, because metastable atoms are neutral in charge, the charge of a precursor will have little, if any, effect on the collision frequency. A simple protonated peptide will be considered below to illustrate the selective chemistry expected to follow metastable-atom activation. Scheme 1 shows a McLafferty-type rearrangement for protonated dialanine. This reaction occurs via hydrogen transfer from the γ-position followed by bond cleavage of the β-bond. The reaction is simplified as a concerted mechanism below. All of the commonly occurring amino acids—with the exception of glycine—have a hydrogen in the γ-position and could fragment through this common pathway.

Scheme 1. Possible outcome from Penning ionization of dialanine: PI leads to a radical cation on the carbonyl oxygen atom, which follows a McLafferty-type rearrangement to provide β-cleavage of the amide backbone.

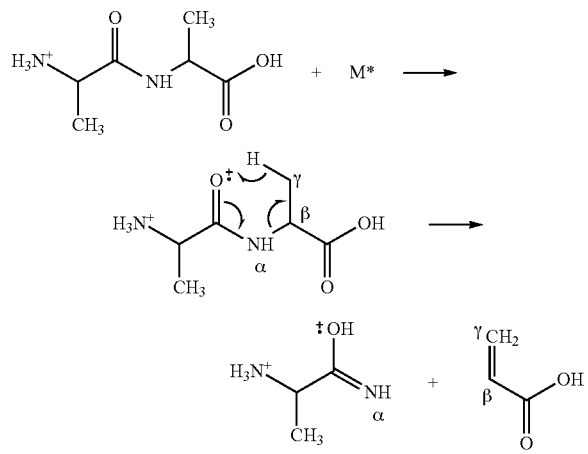

Scheme 1. Possible outcome from Penning ionization of dialanine: PI leads to a radical cation on the carbonyl oxygen atom, which follows a McLafferty-type rearrangement to provide β-cleavage of the amide backbone.

Scheme 2 shows another favored pathway for the rearrangement/fragmentation of radical cations. This fragmentation occurs via α-cleavage.

Scheme 2. Alternative outcome from Penning ionization of dialanine: PI leads to a radical cation on the carbonyl oxygen atom, which fragments through α-cleavage of the amide backbone.

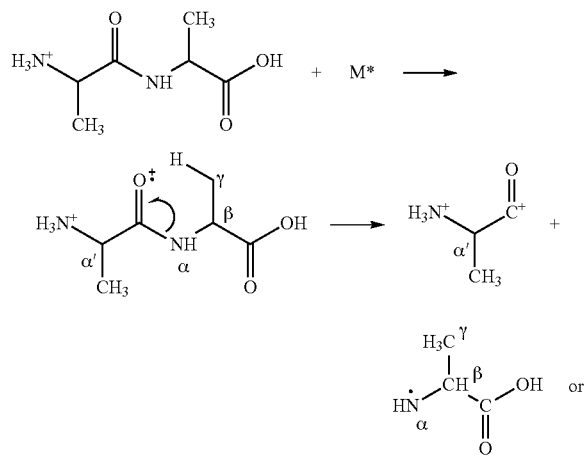

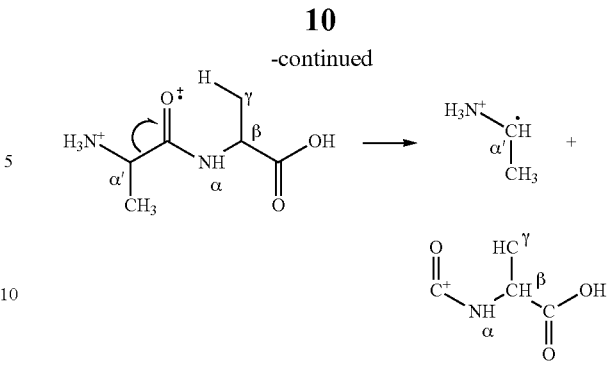

Scheme 2. Alternative outcome from Penning ionization of dialanine: PI leads to a radical cation on the carbonyl oxygen atom, which fragments through α-cleavage of the amide backbone.

Schemes 1 and 2 show that the expected rearrangement/fragmentation pathways of metastable activation will result in cleavage of the amide backbone. Amide backbone cleavage is the key to sequencing peptides and proteins using mass spectrometry. The reaction products generated by the rearrangement/fragmentation of the dipeptide above would provide all the information necessary to sequence the precursor molecule. The distribution of proton and electron-hole charges between products obviously will depend on the pathway taken—McLafferty rearrangement or α-cleavage—but will also depend heavily on the location of the proton prior to metastable activation. One can clearly see in Scheme 2 that in some cases it will be possible to observe two charged products from a singly-charged precursor ion. This is a significant possibility, and one that could dramatically improve the signal intensities and limits of detection in tandem mass spectra.

Sequencing polypeptides using this technology relies on the correct interpretation of fragmentation spectra. The spectra obtained via the new fragmentation method of MAD-MS is expected to follow the same principles and the same methods of nomenclature that are used to interpret the product ion spectra of any other fragmentation method. These methods rely on the fact that fragmentation can, and often does, occur at quite random amino-acid positions on each peptide ion that is fragmented. If enough ions are fragmented, one will obtain a distribution of fragmentation product ions containing all the possible fragmentation positions. The differences in mass between certain peaks in the product-ion mass spectra relates to the masses of the amino acid residues at those points, and thus a 'ladder' of amino acid residues can be generated for the peptide ion in question. Product ion spectra obtained via MAD-MS should be searchable in any of the databases that are already established for the assignment of CAD product-ion spectra. Therefore, the new technology is expected to fit seamlessly into existing protocols for data analysis.

Similar to ECD, we expect the transfer of energy from metastable atoms to larger peptides and proteins to be a nonergodic reaction. That is, the excess energy deposited from a metastable atom to a bio-ion during ionization will not have time to equilibrate over all the internal energy modes in the bio-ion. Instead, the energy will go into fragmenting the bio-ion close to the site of 'impact'. This hypothesis is supported by several facts: 1) ECD of peptides and proteins has recently been shown to be nonergodic; 2) Recent investigation have demonstrated that when self assembled monolayers (SAMs) are exposed to metastable atoms fragmentation takes place at the site of impact. Therefore, collisions between large proteins and metastable atoms would be expected to cause localized destruction of the protein surfaces, in a nonergodic process, and especially through pathways such as those described in Schemes 1 and 2.

Unlike current activation methods, the method of energy transfer described herein is independent of the mass of the precursor ion. In many tandem mass spectrometers, ions are accelerated using static or dynamic electric fields to encourage higher-energy collisions with inert targets. When a small ion collides with a gas such as helium, the kinetic energy can be converted to internal energy quite effectively. However, for large molecules, the transfer of energy is much less efficient. This is the main reason why large biomolecules have been so difficult to fragment using collisional technologies. In ECD and metastable-activated dissociation the mode of energy transfer is independent of the mass of the precursor ion. This is one reason why ECD has proven to be so beneficial for structural characterization of larger peptides and proteins. We therefore expect metastable activation to function as effectively for larger peptides and proteins as it would for small molecules.

An additional benefit of metastable activation is highlighted in Schemes 1 and 2. That is, each metastable impact may generate a new charge on the precursor ion. Therefore, the more exposure a precursor ion has to metastable atoms, the more product ions can be generated from that precursor. This possibility could dramatically enhance the ability to observe and interpret post-fragmentation spectra of proteins and peptides. This improvement could permit smaller sample sizes of proteins to be sequenced in a top-down manner without the requirement for enzymatic digestions. This would obviate the need for multiple wet-chemistry steps and could make the identification of proteins easier and faster than is currently possible.

Metastable-activated dissociation is expected to reveal surface active residues and functional groups of proteins and macromolecules with three-dimensional structure in the gas phase. This could help elucidate the three-dimensional structure and folding of biomolecules. For example, large proteins can have complicated three-dimensional structure that can be thought of as a tightly knotted rope. Due to the method of energy transfer from metastable atoms to target compounds, the activation method described herein may only activate molecular orbitals present at the very outermost surface of the protein. Therefore, only those amino acid residues exposed at the surface of the protein during initial activation will be selectively fragmented. This is similar to using scissors to cut only the exposed loops of the knotted rope. In some cases, simply 'cutting' the amide backbone at the surface will not be enough for a mass spectrometer to determine where the protein was cut: the protein will need to be 'untied' so that the m/z ratios of the products can be used to identify where the original protein was cut. In this scenario, conventional collision-activated dissociation could be used in concert with metastable activation to facilitate the 'untying' of the peptide products. In addition to the conformational information elucidated in this manner, exposing the peptide fragmentation products to additional activation with metastable atoms could provide sequence information and/or post translational modification information.

The examples described herein are for illustrative purposes only and are not meant to limit the scope of the invention as defined in the claims.

What is claimed is:

1. A method for determining a conformational state of gas phase ions, comprising:
   selecting or identifying a precursor ion or product ion of interest with at least one ion mobility device;
   wherein metastable atoms are used to induce a change in a conformation or structure of the ions.

2. The method of claim 1, wherein a relative intensity of the ion is correlated with a probability of interaction with the metastable atoms, and wherein an increased intensity indicates that the ion is from a surface or exposed site.

3. The method of claim 1, wherein the precursor ion is selected using an ion mobility device, fragmented using a metastable atom, and analyzed using a second ion mobility device.

4. The method of claim 3, wherein the mobility devices can be operated in a method selected from the group consisting of low field, high field, asymmetric field (FAIMS), traveling wave, and differential field mobility (DMS).

5. The method of claim 1, wherein the precursor ion is selected using an ion mobility device and analyzed using a mass spectrometer device.

6. The method of claim 1, wherein the precursor ion is selected according to their mass to charge ratio using a mass spectrometer and analyzed using an ion mobility device.

7. The method of claim 1, wherein the precursor ion is selected according to their mass to charge ratio using a mass spectrometer and analyzed using a combination of ion mobility and mass spectrometry devices.

8. The method of claim 1, wherein the precursor ion has at least one positive or negative charge and is fragmented or modified by exposure to metastable atoms.

9. The method of claim 1, wherein any of the product ions generated via metastable activation can be subsequently fragmented using a second activation method to release the primary product ions or generate secondary product ions.

10. The method of claim 9, wherein the activation method for the release of primary ions or generation of secondary ions is selected from the group consisting of infra-red multiphoton dissociation (IRMPD), laser-induced dissociation (LID), UV-induced dissociation, collisional activation, ion-ion reactions, ion molecule reactions or electron capture, and electron transfer reactions.

* * * * *